US007918654B2

(12) United States Patent
Adahan

(10) Patent No.: US 7,918,654 B2
(45) Date of Patent: *Apr. 5, 2011

(54) COMPACT VACUUM PUMP

(76) Inventor: Carmeli Adahan, Jerusalem (IL)

( * ) Notice: Subject to any disclaimer, the term of this patent is extended or adjusted under 35 U.S.C. 154(b) by 0 days.

This patent is subject to a terminal disclaimer.

(21) Appl. No.: 11/896,674

(22) Filed: Sep. 5, 2007

(65) Prior Publication Data

US 2007/0297924 A1    Dec. 27, 2007

Related U.S. Application Data

(63) Continuation of application No. 11/797,555, filed on May 4, 2007, now abandoned, which is a continuation of application No. 11/710,494, filed on Feb. 26, 2007, now abandoned, which is a continuation of application No. 11/529,388, filed on Sep. 29, 2006, now Pat. No. 7,758,539, which is a continuation of application No. 10/486,940, filed on Feb. 13, 2004, now Pat. No. 7,284,965, which is a continuation of application No. PCT/IL02/000661, filed on Aug. 12, 2002.

(30) Foreign Application Priority Data

Aug. 14, 2001 (GB) .................................. 0119811.8

(51) Int. Cl.
*F04B 17/03* (2006.01)
*F04B 17/06* (2006.01)
(52) U.S. Cl. .......... 417/360; 417/313; 604/35; 604/151; 604/153
(58) Field of Classification Search .................. 417/313, 417/360; 604/30, 35, 151–153
See application file for complete search history.

(56) References Cited

U.S. PATENT DOCUMENTS

| 3,811,803 | A | | 5/1974 | Frohberg |
| 3,981,636 | A | | 9/1976 | Aoki et al. |
| 4,231,722 | A | | 11/1980 | Teichmann |
| 4,468,222 | A | * | 8/1984 | Lundquist .................... 604/153 |
| 4,570,833 | A | | 2/1986 | Vanderjagt |
| 4,635,621 | A | | 1/1987 | Atkinson |
| 4,639,245 | A | | 1/1987 | Pastrone et al. |
| 4,681,562 | A | | 7/1987 | Beck et al. |

(Continued)

FOREIGN PATENT DOCUMENTS

| EP | 0 307 069 | 3/1989 |
| EP | 0 494 375 | 7/1992 |
| EP | 0 669 463 | 8/1995 |

(Continued)

*Primary Examiner* — Devon C Kramer
*Assistant Examiner* — Patrick Hamo
(74) *Attorney, Agent, or Firm* — The Nath Law Group; Susanne M. Hopkins; William L. Klima

(57) ABSTRACT

A vacuum pump capable of pumping solid, liquid and gas, or any combination thereof, including a drive (40) and a manually disengageable pumping system connected thereto. The pumping system is composed of a two- or three-chambered canister (1, 18, 21) within which solids, liquids, and gases can be separated from one another. A highly flexible diaphragm (24) attached to the canister and sealed against it circumferentially, facilitates this separation, when reciprocating and pumping. The components of the pumping system are designed to be disposable, and the two- or three-chambered canister provides for a highly efficient pumping system that is significantly smaller in size than those previously known. The pump is particularly useful for medical applications.

18 Claims, 3 Drawing Sheets

U.S. PATENT DOCUMENTS

| | | | |
|---|---|---|---|
| 4,747,843 A | 5/1988 | Felix et al. | |
| 4,798,589 A | 1/1989 | Tseo | |
| 4,828,464 A | 5/1989 | Maier et al. | |
| 4,842,584 A | 6/1989 | Pastrone | |
| 4,883,476 A | 11/1989 | Kurtz et al. | |
| 5,021,048 A | 6/1991 | Buckholtz | |
| 5,173,033 A | 12/1992 | Adahan | |
| 5,466,229 A | 11/1995 | Elson et al. | |
| 5,645,540 A * | 7/1997 | Henniges et al. | 604/320 |
| 6,135,725 A | 10/2000 | Chou | |
| 6,213,727 B1 | 4/2001 | Kawaguchi | |
| 6,315,534 B1 * | 11/2001 | Chou | 417/550 |

FOREIGN PATENT DOCUMENTS

| | | |
|---|---|---|
| EP | 1 045 146 | 10/2000 |
| GB | 2 124 712 | 2/1984 |
| JP | S52-52465 | 11/1977 |
| JP | 56-90486 | 12/1979 |
| JP | 55-35118 | 12/1980 |
| JP | 60-127489 | 8/1985 |
| JP | 61-168366 | 7/1986 |
| JP | 62-98864 | 6/1987 |
| JP | 05-231329 | 7/1993 |
| JP | 56-27384 | 7/1996 |
| JP | 2505726 | 7/1996 |

* cited by examiner

COMPACT VACUUM PUMP

This is a Continuation of U.S. patent application Ser. No. 11/797,555, filed May 4, 2007 which is a Continuation of U.S. patent application Ser. No. 11/710,494 filed Feb. 26, 2007, which is a Continuation of U.S. patent application Ser. No. 11/529,388 filed Sep. 29, 2006, which is a Continuation of U.S. patent application Ser. No. 10/486,940 filed Feb. 13, 2004, which is a continuation of International Patent Application No. PCT/IL02/00661 filed Aug. 12, 2002 which claims priority to United Kingdom patent application no. 0119811.8 filed on Aug. 14, 2001, the entire contents of which is hereby incorporated by reference in its entirety.

The present invention relates to a vacuum pump, especially useful in the field of medicine. More specifically, the pump disclosed herein includes a drive and a disposable pumping system that can be easily disengaged from the drive after use to allow for easy disposal of all pump components which come into contact with the matter being suctioned, together with the contained matter. The pump is not limited in the volume of matter it is capable of suctioned while maintaining uninterrupted vacuum pressure. During medical surgery or emergency airway clearing body fluids, such as blood or emesis, are suctioned. Vacuum pumps are utilized to generate vacuum inside a suction canister into which the body fluids are drawn through a tube, called a "suction catheter." Conventional vacuum pumps, also termed "aspirators" in medicine, contain rigid vacuum canisters into which the suctioned fluids are collected that maintain their shape and stiffness under high vacuum pressure. Some suction canisters are disposable and others can be removed for cleaning, disinfection, and re-use.

Aspirators of the type described above are characterized by a number of disadvantages, including the following:
1. When a large volume of fluid is collected, the suction canisters have to be relatively large in volume. Most commonly a canister of up to five liters in volume is used. Large canisters slow the vacuum rise rate because of the large air volume to be removed from the canister before a vacuum is created in the canister strong enough to draw the suctioned matter.
2. Since the air in the suction canister is drawn through the pump, it is very difficult to prevent contamination of the non-disposable pump components, such as the diaphragm, valves, cylinder or piston, even when the suction canister is disposed of after use. Contaminated pumps are a health hazard as the air flowing through them is exhausted to the atmosphere.
3. Aspirators are used for drawing body fluids and emesis, which may contain solids. Air is also drawn into the pump, during aspiration. Vacuum pumps are generally efficient in pumping either air or fluids, but most pumps are inefficient in pumping all three types of matter.

Thus, conventional vacuum devices are large, bulky, costly and inefficient in performing their function.

In the present invention the term "pumping system" generally refers to a system having the following components: a suction canister, a suction inlet, a waste outlet, and integral means for creating suction. The term "disposable vacuum pump" generally refers to a pump in which all components other than the drive are inexpensive, and therefore may be disposed of. One wishing to re-use the disposable components (or use similar, non-disposable components) may, however, do so. The term "drive" generally refers to a pump component included of an electric motor, or to other means by which a pump piston, or a diaphragm, may be caused to reciprocate while contained within a housing. The term "body fluids" refers to blood, emesis or mucus. The term "three types of matter," "three types of media," and "three states of matter" refer to liquid, solid and gas. The terms "matter," "media," and "material" are used interchangeably to refer to the material being suctioned.

Embodiments of the invention may provide an improved vacuum pump capable of pumping air or gas, liquid and solids, and capable of separating the three types of matter to allow efficient pumping while collecting the liquid in a low cost bag.

Further embodiments may provide a pump in which all components that come in contact with body matter, or any other pumped media, can be easily disconnected and removed from the pump's drive means to be sterilized or disposed of. This leaves the non-disposable drive free from contamination. In prior-art pumps that have disposable canisters, the suctioned air is drawn through the pump, bringing the inside of the pump in contact with air that may be contaminated. The inside of the pump is traditionally not accessible for cleaning.

Embodiments of the present invention may further provide a vacuum pump which is extremely fast in generating a high vacuum or suction pressure yet do so with a relatively small vacuum canister and a low capacity pump.

It is further desirable to provide a physically compact vacuum pump with performance and capacity that are independent of its dimensions and are significantly higher than those of physically larger vacuum pumps. In addition, it is desirable to provide a vacuum pump which generates uninterrupted vacuum, independent of the volume of the vacuum canister that does not fill up as do conventional vacuum canisters.

The vacuum pump includes a drive and a disposable pumping system connected to this drive and adapted to be manually disengaged therefrom, wherein the disposable pumping system includes:
(a) a three-chambered canister, wherein an inlet leads into the first chamber, and the first chamber has means for retaining solids and preventing their passage from the first chamber to the second chamber; and the second chamber has a one-way valve at its exit, the valve allowing passage of liquid and gas out of the second chamber; and the third chamber has an outlet for the discharge of air, and an additional outlet for the discharge of liquid; and the third chamber further has a one-way valve at its inlet allowing entry of liquid and gas through the valve while preventing exit of matter through the valve;
(b) a highly flexible diaphragm, attached to the three-chambered canister, sealing against it circumferentially, wherein the flexible diaphragm is attached to a partition with the three-chambered canister, in which the valves are installed;
(c) a drive member attached to the diaphragm, wherein reciprocation of the drive member induces reciprocation of the diaphragm; and
(d) means for mounting and engaging the disposable pumping system to the housing of a drive, wherein the means are capable of simultaneously coupling the pump drive member to the drive.

The drive is coupled to the drive member, and the drive includes an electric motor rotating a crank, the crank being connected to reciprocating means, in such a way that activation of the drive induces reciprocation of the crank and of the drive member. The pumping system is capable of being attached or detached from the drive in a rapid and facile manner (in the preferred embodiment, accomplished by a single, simple, wrist twist motion).

According to preferred embodiment of the present invention, the three-chambered canister has a volume of approximately 100 cc.

Further according to a preferred embodiment of the present invention, the pump includes a vacuum port outlet present in the second chamber, the outlet connected by tubing to an external vacuum gauge for the purpose of monitoring the pressure inside the first and second chambers.

Additionally, according to a preferred embodiment of the present invention, the means for retaining solids in the first chamber are included of a sieve.

Moreover, according to preferred embodiment of the present invention, the highly flexible diaphragm is capable of yielding or stretching when large quantities of fluid are contained within it. When subjected to high loads, the diaphragm is capable of stretching to effectively reciprocate only a fraction of its area (such as 50%) while the remainder of its surface remains stationary.

Still further, according to preferred embodiments of the present invention, the vacuum pump additionally includes means for sealing the three-chambered canister and preventing leakage of air or materials into or out of the canister, as well as further preventing loss of vacuum in first and second chambers.

According to embodiments of the present invention, the pump additionally includes a disposable waste container for collection of discharged liquid that is attached to the liquid outlet of the third chamber. In a preferred embodiment, the disposable waste container is a waste bag, having any appropriate size. In some preferred embodiments, the capacity of the waste bag is between 500 cc and 5 liters. The waste-collection bag is a low cost waste container, at ambient pressure, which is easily disposed of along with the body fluids it contains, together with the pumping system.

Furthermore, according to the preferred embodiment of the present invention, the means for mounting and engaging the pumping system to the drive housing include a mounting base protruding from the lower portion of the three-chambered canister, the mounting base adapted for mating and attaching to the drive housing. In the preferred embodiment, twisting of the mounting base against the drive housing or mating portion thereof couples the two physically.

Still further yet, according to the preferred embodiment of the present invention, the drive rotates a crank, and a reciprocating rod receptacle is connected to the crank, and the rod receptacle is adapted to mate with the drive member. In the preferred embodiment, a lock clip secures the drive member to the rod receptacle. Coupling the mounting base to the drive housing is affected simultaneously with the securing of the drive member to the rod receptacle, in a single operation.

Additionally, the pumping system and the drive may be portable and may be operated on battery power.

Moreover, the pumping system additionally includes means for sealing the pumping system, for facilitating disposal of the pumping system, with all pumped matter contained. Further according to preferred embodiments of the present invention, the pump is capable of generating continuous flow of matter therethrough, while maintaining uninterrupted vacuum pressure.

The pump may be capable of generating a vacuum pressure of approximately 650 mm of Mercury as measured in the first and second chambers.

Additionally, in a preferred embodiment, the pump further includes suction catheter tubing attached to the inlet present in the first chamber, allowing entry of matter into the three-chambered canister.

Unlike common diaphragm pumps, the diaphragm in this invention is flexible and not restrained by a rigid piston. The flexibility of the diaphragm allows it to stretch and conform to the pumped matter, irrespective of the reciprocal motion of the rigid drive member. Thus, when the diaphragm encounters resistance it stretches and yields, allowing uninterrupted motion of the reciprocating drive member.

The three-chambered canister, the diaphragm and the one-way valves advantageously include an integral pumping system that can easily be attached to a drive that causes the drive member to reciprocate. Such a drive, as described, may be an electric motor, whose output shaft has a crank to which the drive member is connected. The electric motor will thus, when powered, affect pumping from one chamber of the canister to the other. The pumping system can easily be disengaged from the drive after use, and be sterilized or disposed of. The ability to completely separate the heart of the pump and its associated chambers and tubing conduits from the drive motor allows disposal or sterilization of all pump components that come in contact with pumped matter. It would be obvious to those skilled in the art that means other than an electric motor may be utilized to induce the reciprocal motion of the drive member.

The three-chambered canister is constructed in a manner such that the solids entering the chamber are trapped and prevented from entering further into the pump and affecting its performance by blocking the valves and tubing. It would be obvious to those skilled in the art that when the pumped matter is not likely to include solids, there would be no need to prevent them from reaching the pump's one-way valves, and thus the pumping system hereby described would function equally well without the first chamber. A pump having only two chambers, to be used in such case, is thus described below as well. Additionally, the pumped air is separated from the fluid and released to the atmosphere so that liquid, and not air, is collected in the waste bag, thereby utilizing the volume of the waste bag efficiently. Thus, the capacity of the pump to suck or collect fluids is not limited by the size of the chamber into which the fluid is drawn, and even a small chamber can be utilized to pump large volumes of fluid, limited only by the capacity of the waste bag. This is in contrast to pumps of the prior art in which the canister or chamber size limits the amount of matter that may be suctioned, and when large canisters are used to overcome this limitation evacuating the large canister by the pump then becomes a slow process.

The present invention can be utilized in the field of medicine, to aspirate body fluids, emesis and mucous; however, the scope of the invention is not limited to medical use alone, and the vacuum pump may be utilized in other fields as well. An important feature of the pump is the ability to easily and economically remove and replace all components that come in contact with the materials being pumped, thus preventing any harmful contamination. The pump can therefore find application in the field of chemistry as well, where prior art pumps are difficult to clean after use.

In addition, there is provided in an alternative aspect of the present invention a vacuum pump for the pumping of liquid and gas (preferably not for use in pumping of solids), including a drive, and a manually disengageable disposable pumping system connected to the drive, wherein the disposable pumping system includes:

a) a dual-chambered canister, wherein the first chamber has an inlet and a one-way valve at the exit of the first chamber, the valve allowing passage of liquid and gas out of the first chamber; and the second chamber has an outlet for the discharge of air, and an additional outlet for the discharge of liquid; and the second chamber is further connected via a one-valve, allowing entrance of liquid or gas through the valve, while preventing exit of liquid or gas through the valve;

b) a highly flexible diaphragm, attached to the dual-chambered canister sealing against it circumferentially, wherein the flexible diaphragm is attached to a partition with the dual-chambered canister in which the valves are installed;

c) a drive member attached to the diaphragm, reciprocation of the drive member inducing reciprocation of the diaphragm; and d) means for mounting and engaging the disposable pumping system to the housing of a drive, wherein the means are capable of simultaneously coupling the drive member to the drive.

In the vacuum pump the drive is coupled to the pumping system so that activation of the drive induces reciprocation of the flexible diaphragm, and the pumping system is capable of being attached or detached from the drive in a rapid and facile manner.

It will be clear to those skilled in the art that while the preferred embodiment of the invention includes several features, partial application of the disclosed features of the invention does not limit the scope of the invention. For instance, the diaphragm may be substituted by a piston for pumping, the discharge port may function in the absence of the waste bag and the liquid and gas outlets may be combined into a single outlet.

BRIEF DESCRIPTION OF THE DRAWINGS

For a better understanding of the invention, embodiments of it will now be described by way of example, with reference to the accompanying drawings in which.

DETAILED DESCRIPTION OF THE INVENTION

It is appreciated that the detailed description that follows is intended only to illustrate certain preferred embodiments of the present invention. It is in no way intended to limit the scope of the invention, as set out in the claims.

Figure 1:
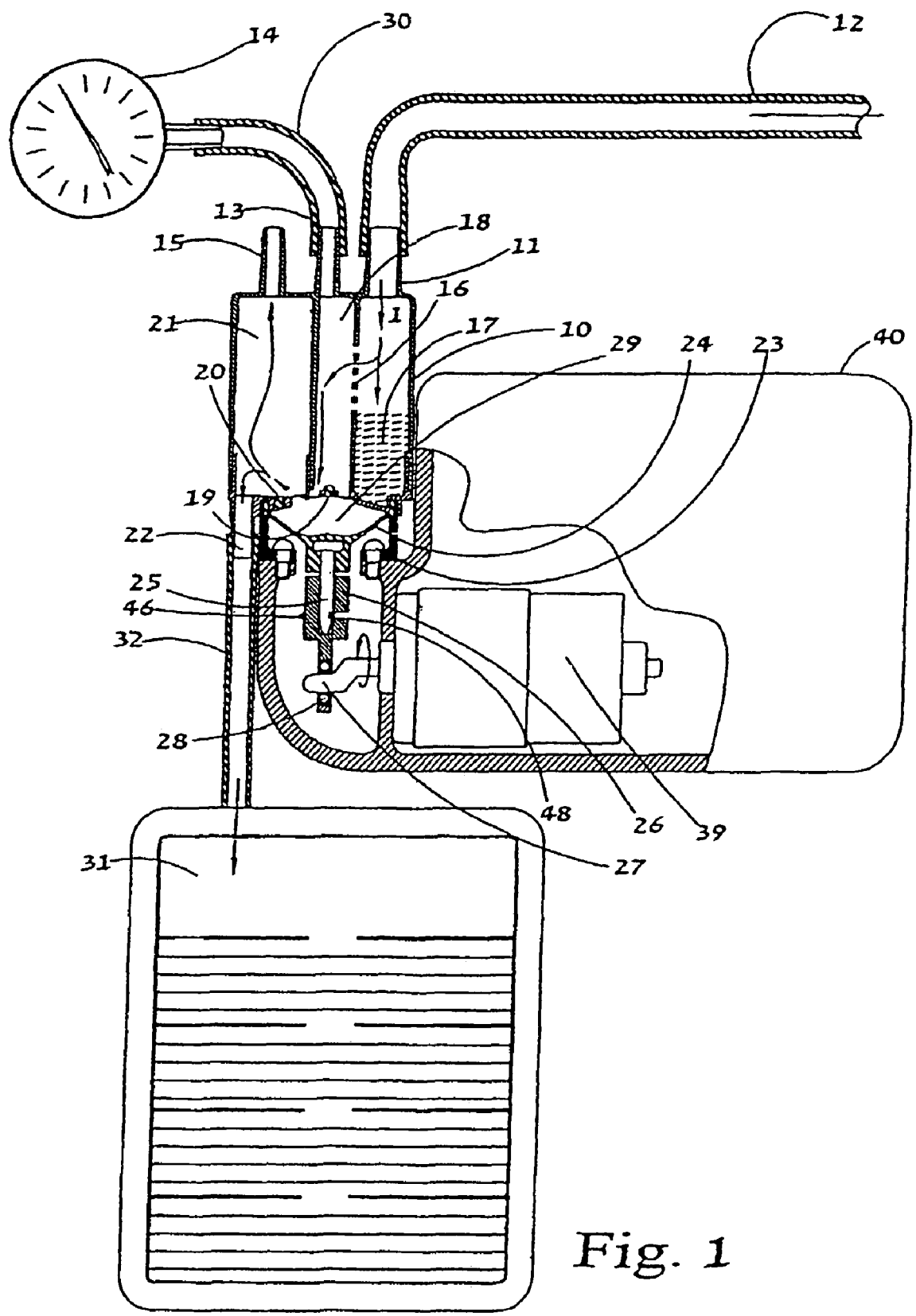
FIG. 1 is a cross-sectional view of a preferred disposable vacuum pump having a three-chambered canister connected to a waste bag, wherein the suction is created by reciprocating a diaphragm by an electric motor drive.

Referring now to FIG. 1, there is provided a vacuum pump containing a three-chambered canister 10, which is employed for the performance of several different functions. The three-chambered canister 10 has an inlet 11 in its first chamber 1. A suction tube catheter 12 is connected to the inlet 11. In the second chamber 18 a vacuum outlet port 13 is connected to a vacuum gauge 14. In the third chamber 21 an air discharge outlet 15 is present, which is open to the atmosphere. The first chamber 1 contains a sieve 16, utilized to prevent solids 17 from entering the second chamber 18, also termed the "liquid chamber." Two one-way umbrella valves 19 and 20 are present in the bottom of the second chamber 18 and the third chamber 21, respectively. The third chamber 21 is at ambient pressure, and has a liquid outlet 22. To the bottom of the three-chambered canister 10 there is attached a mounting base 23, used to mount the canister and its associated tubing 12 onto the drive housing 40 or on a docking means connected to the drive housing. The mounting base 23 is also utilized to secure a diaphragm 24 to the underside of the three-chambered canister 10. The diaphragm 24 has an integral rod-shaped drive member 25, which is inserted into a corresponding cavity in a receptacle rod 26, pivotally attached to motor 39, via a crank 27 coupled to a bearing 28. Upon activation of the motor 39, the crank 28 is rotated by motor 39, which reciprocates the receptacle rod 26, causing the diaphragm 24 to increase and decrease the volume of the cavity 29 that it forms. This creates a vacuum therein, capable of drawing towards it, and thus pumping, air or fluid that passes through the one-way umbrella valves 19 and 20.

While the preferred embodiment describes a motor-crank combination as the means by which to reciprocate diaphragm 24, it would be apparent that other drive means may be used to create the reciprocal movement of the diaphragm.

Air, liquid and solids may enter the three-chambered canister 10 through a suction tube 12, which may, by way of example, be inserted into a patient's mouth for the removal of emesis. The three states of matter being pumped enter the three-chambered canister 10 through the inlet 11. Solids 17 are prevented from moving further than the first chamber 1 by means of sieve 16. Liquids and air enter the second chamber (liquid chamber) 18, which is under vacuum when diaphragm 24 reciprocates, driving them past one-way umbrella valve 20 into the third chamber 21. The vacuum level in liquid chamber 18 is monitored by a vacuum gauge 14, connected to the vacuum outlet port 13 via a conduit 30. The air and liquid entering the third chamber 21 are separated, whereupon the liquid is drained into waste bag 31 through a drain tube 32, and the air is driven out to atmosphere through an air discharge outlet 15.

From the description above, it is clear that the three-chambered canister 10 is the heart of the pump, to which the diaphragm 24 is attached to perform the pump function together with the one-way umbrella valves 19 and 20. Out of the three-chambers that make up the three-chambered canister, only one, the liquid chamber 18, is under vacuum. The three-chambered canister is partitioned by the sieve 16; the first chamber 1 and the third chamber 21 are essentially at ambient pressure.

The pump hereby described is distinct in its capability to suck liquid, solids and air or any mixture of the three, and to separate each of the three matter types into their respective destinations. The three types of matter are separated in order to prevent clogging of the pump by suctioned solids, and in order to collect only fluid for disposal, and not gas, thus minimizing the volume of the waste material for disposal, and of the canister that holds this waste material. It is also of particular importance to note that air and liquid can be pumped through the pump continuously at any volume, limited only by the volume of the waste bag 31 to contain the pumped liquids.

The pump's ability to pump air and liquid is unlike conventional pumps that are efficient in pumping only one type of matter, and is enhanced by the flexibility of the diaphragm 24. Unlike conventional pump diaphragms, which are rigidified by a piston or ribbing to prevent them from excessive flexing which reduces displacement, the diaphragm 24 described in this invention is particularly flexible so it can yield when encountering heavy loads such as those present when pumping liquid. This diaphragm flexibility also provides an additional substantial advantage: when the vacuum in pumping volume 29 is high the diaphragm 24 stretches to allow the reciprocation of the receptacle rod 26 to occur at minimal burden to the "drive," which in the preferred embodiment includes an electric motor 39.

Figure 2:
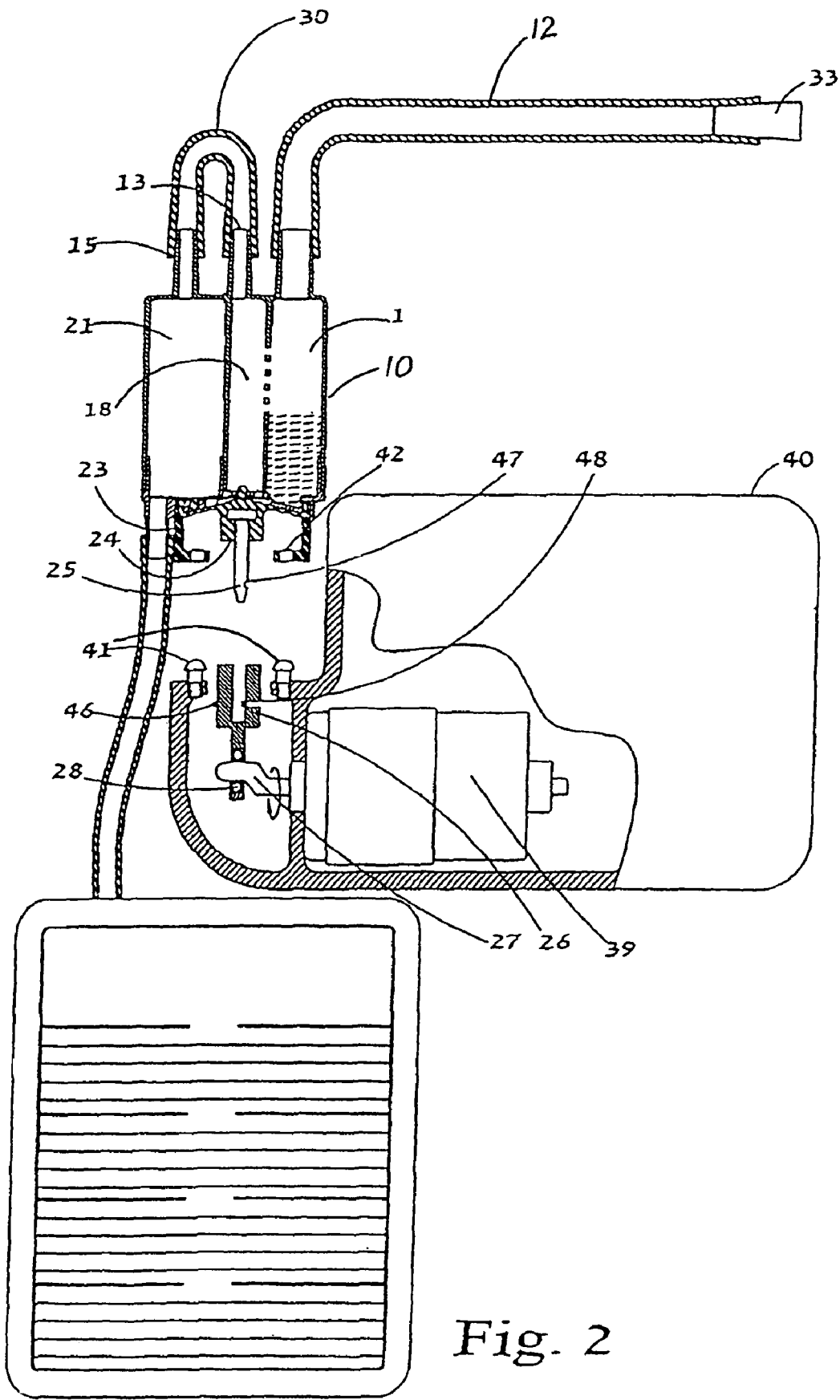
FIG. 2 is a cross-sectional view of the "pumping system" disengaged from the "drive", to be disposed of as one integral unit.

In order to obtain high vacuum levels it is necessary to extract all air from pumping cavity 29 when the diaphragm 24 is at its upper travel extremity, as illustrated in FIG. 2. This function, in a conventional vacuum pump, will cause damage to the pump when liquid or solids enter the pumping chamber, as they cannot be expelled through the pump's outlet valve fast enough. In the disclosed invention, the flexibility of the diaphragm 24 will allow it to yield, or bulge, when encountering resistance as a result of liquid or solid presence, preventing excessive forces and the ensuing damage.

An additional important function of the flexibility of diaphragm 24 is its ability to stretch and yield, so that when the vacuum level in the pumping cavity 29 is high, only a smaller effective area of diaphragm 24 reciprocates, and stretches, requiring less power from motor 39 to effect reciprocation.

In FIG. 2, drive housing 40 that contains the motor 39, crank 27 and reciprocating receptacle rod 26, is shown disengaged from all other parts since the drive will be re-used while all other parts, which have directly contacted the matter being pumped, are slated for disposal and are termed the "disposable pumping system." The disposable pumping system, essentially including the canister, the diaphragm, associated valves, the disposable waste bag, and associated tubing, are shown in FIG. 2 after all outlets have been sealed for disposal. The suction tube 12 is plugged with a plug 33 to prevent any liquid from leaking out of it. The conduit 30 is disengaged from the vacuum gauge 14 (FIG. 1) and attached to the air discharge outlet 15, sealing all possible leak paths from three-chambered canister 10.

It will be appreciated by persons skilled in the art that the drive 40, which is the only non-disposable hardware in the preferred embodiment, does not come into contact with any of the pumped media. This is unlike conventional aspirators or suction pumps that pass the suctioned air through them and may thus be contaminated by infectious air.

Figure 3:
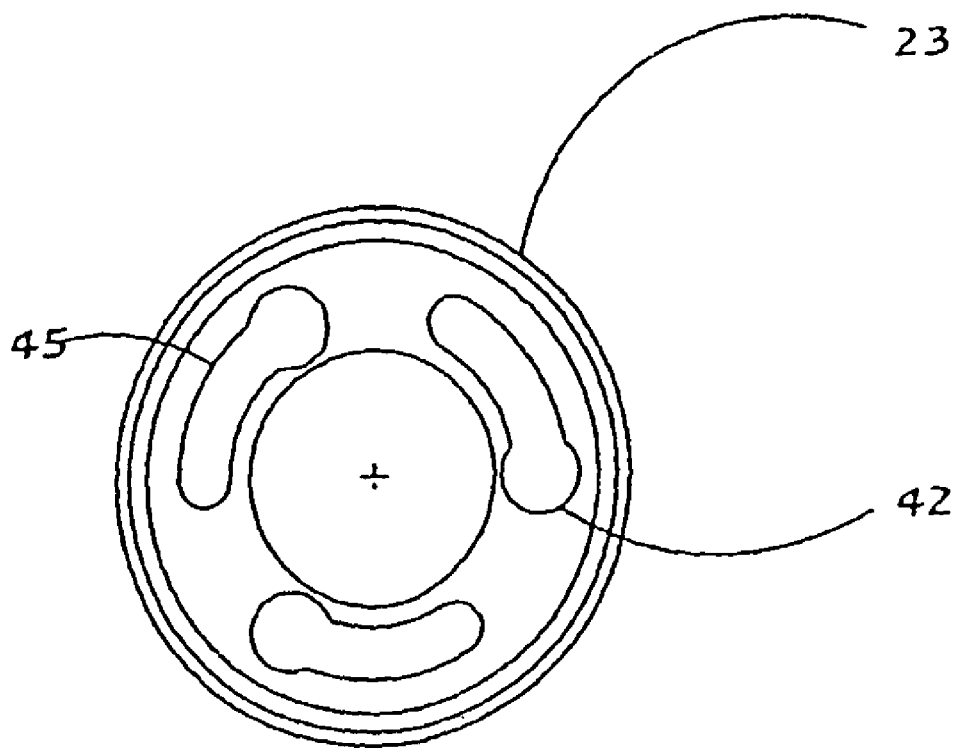
FIG. 3 is a view of a mounting base, with a bayonet arrangement for quick—twist engagement and disengagement of the disposable components.

The method and means for attachment and mounting of the disposable pumping system to drive 40 is illustrated in FIGS. 2 and 3, whereby the mounting base 23 is placed on top of retainers 41 as shown in FIG. 2. The retainers 41 protrude from a shelf- or step-like part of the drive 40 and have large mushroom-shaped heads, which pass through larger openings 42 in a flange of the base 23, seen also in FIG. 3. When the three-chambered canister 10 is rotated clockwise with its mounting base 23, the large heads of the retainers 41 engage slots 45 (FIG. 3), attaching the mounting base 23 to the drive 40 in a bayonet-type fastening action using a 45-degree twist. This action is similar to attaching a cap to a glass jar. The drive member 25, shown in FIGS. 1 and 2, is inserted into the receptacle rod 26 simultaneously with the attachment of the mounting base 23 to drive housing 40.

Figure 4:
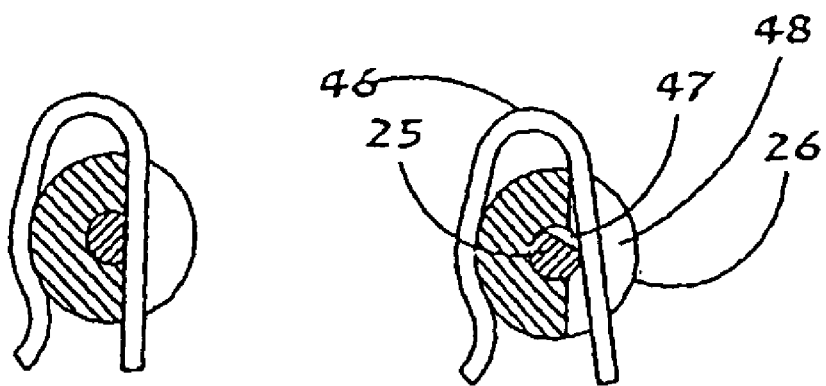
FIG. 4 is a cross-sectional view of the locking mechanism, utilized to attach the pump drive member to the receptacle rod of the electric motor.

Referring to FIG. 4, a spring-loaded lock-clip 46 keys and locks the drive member 25 to the receptacle rod 26, when the lock clip engages pre-aligned slots 48 present in the drive member 25 and the receptacle rod 26. The disengagement of the mounting base 23 from the drive 40 is effected, simultaneously with disengagement of the drive member 25 from the receptacle rod 26, when both are rotated counterclockwise, by drive member 25 pushing lock clip 46 out of its slot 47, as illustrated in FIG. 4, eliminating the keying between drive member 25 and receptacle rod 26. This action is similar to the removal of a cap from a jar by twisting counterclockwise and lifting.

While only one form of engagement of canister 10 to drive 40 was described in the preferred embodiment of this invention, it would be clear to those skilled in the art that other similar methods for quick fastening of these parts can be utilized effectively.

The above-described method of engagement has, however, an important feature that should be noted. Since the receptacle rod 26 may be at its lower position at the time when the drive member 25 is inserted into it, slots 47 and 48 may come into alignment only when motor 39 is powered and crank 27 (FIGS. 1 and 2) raises receptacle rod 26 allowing lock clip 46 to key slots 47 and 48. Thus, the insertion of drive member 25 into receptacle rod 26 enables engagement, rather than fastening the two together.

It will be appreciated by persons skilled in the art that the present invention is not limited by what has been shown and described hereinabove, merely by way of example. Rather, the scope of the present invention is limited solely by the claims, which follow:

The invention claimed is:

1. A pumping apparatus for pumping a fluid, comprising:
   (A) a pump drive unit, comprising a motor accommodated in a drive unit housing;
   (B) a disposable pump unit including a pump base, a pumping chamber and a pump member, said pumping chamber being adapted to expand and contract for pumping by two-way forced reciprocation of said pump member, and further comprising one-way inlet and one-way outlet valves to said pumping chamber, said inlet and outlet valves being operable to alternately open and close by action of said fluid pumped through said chamber responsive to said reciprocation, wherein said pump member is fixedly attached to said pump base to define therebetween said pumping chamber, wherein said attachment is independent of said pump drive unit; and
   (C) mechanical coupling for reversibly mechanically coupling said pump base with said drive unit housing, wherein said motor and said pump member are configured so that attaching said pump base to said drive unit housing via said mechanical coupling brings said pump member and said motor to a position wherein operation of said drive unit results in engagement between said motor and said pump member, and providing for said reciprocation of said pump member by means of said drive unit;
   wherein said pump drive unit is configured for operation as a non-disposable unit, wherein said disposable pump unit is removed from said pump drive unit after use and allowing for further operation of said pump drive unit with a replacement disposable pump unit.

2. The apparatus according to claim 1, further comprising a ventilation opening allowing gas passage between the pump unit and the atmosphere during operation of said pump unit.

3. The apparatus according to claim 1, further comprising disposable tubing coupled to said pump unit.

4. The apparatus according to claim 1, wherein said drive unit comprises a driving element, and wherein said pump unit and said drive unit are constructed so that attaching said pump unit to said drive unit brings said pump member and said driving element to a position providing, during operation of said drive unit, for their engagement and reciprocation of said pump member by means of said driving element.

5. The apparatus according to claim 1, wherein said drive unit comprises first attachment means and said pump unit comprises second attachment means, the two attachment means allowing said attaching of the pump unit to the drive unit by a simple manipulation without tools.

6. The apparatus according to claim 5, wherein said pump unit and said drive unit are constructed so that said first and second attachment means provide detachment of said drive unit from said pump unit by a manipulation including at the most manual unfastening without tools and one detaching motion, and the same detaching motion disengages said pump member from said driving element.

7. The apparatus according to claim 4, wherein said driving element of the drive unit is a reciprocating element adapted for said engagement to said reciprocable pump member by said mechanical coupling.

8. The apparatus according to claim 7, wherein said drive unit comprises an eccentric rotary shaft with a crank adapted to reciprocate said reciprocating element.

9. The apparatus according to claim 7 wherein said coupling includes a rod in one of said reciprocating element and pump member, and a receptacle in the other of said reciprocating element and pump member, said rod and said receptacle being adapted for locking to each other by a fastener, thereby providing said engagement.

10. The apparatus according to claim 9, wherein said rod is adapted to enter said receptacle during said attaching of said pump unit to said drive unit, and is further adapted to be locked by said fastener within one cycle of reciprocation.

11. An attachable and detachable disposable pump unit for use with a non-disposable pump drive unit, wherein the pump drive unit comprises a motor accommodated in a drive unit housing, the pump unit comprising:

a pump base, a pumping chamber and a pump member, said pumping chamber being adapted to expand and contract for pumping by two-way forced reciprocation of said pump member, and further comprising one-way inlet and one-way outlet valves to said pumping chamber, said inlet and outlet valves being operable to alternately open and close by action of a fluid pumped through said chamber responsive to said reciprocation, wherein said pump member is fixedly attached to said pump base to define therebetween said pumping chamber, wherein said attachment is independent of the pump drive unit; and wherein said pump unit includes at least a portion of a mechanical coupling for reversibly mechanically coupling said pump base with the drive unit housing, wherein said motor and said pump member are configured so that attaching said pump base to said drive unit housing via said mechanical coupling brings said pump member and said motor to a position wherein operation of said drive unit results in engagement between said motor and said pump member, and providing for said reciprocation of said pump member by means of the drive unit.

12. The pump unit of claim 11, further comprising a ventilation opening allowing gas passage between the pump unit and the atmosphere during operation of said pump unit.

13. The pump unit of claim 11, wherein said pump unit comprises a pump portion defining a pump inlet and a pump outlet, and a surface defining another part of said pumping chamber, and wherein said pump member comprises a flexible diaphragm.

14. The pump unit of claim 13, wherein said flexible diaphragm is sealed to said pump portion around a circumference of said diaphragm.

15. The pump unit of claim 13, wherein said pump unit comprises a first chamber having a first chamber inlet and a first chamber outlet, said first chamber outlet connected to said pump inlet, and further comprising a second chamber having a second chamber inlet and a second chamber outlet, said second chamber outlet connected to said pump outlet.

16. The pump unit of claim 15 wherein said first chamber and said second chamber are formed with said pump portion.

17. The pump unit of claim 15, wherein said first chamber further comprises an additional second chamber outlet not connected to said pump inlet or to said pump outlet.

18. The pump unit of claim 15, wherein said pump unit is made from plastic material.

\* \* \* \* \*